(12) United States Patent
Choe et al.

(10) Patent No.: US 11,640,663 B1
(45) Date of Patent: May 2, 2023

(54) METHOD OF DETERMINING SUITABILITY OF SKIN ANALYSIS IMAGE AND APPARATUS THEREFOR

(71) Applicant: LULULAB INC., Seoul (KR)

(72) Inventors: Yongjoon Choe, Seoul (KR); Se Min Kim, Ansan-si (KR); Ju Hwan Lee, Seoul (KR); Jong Ha Lee, Hwaseong-si (KR); Sang Wook Yoo, Seoul (KR)

(73) Assignee: LULULAB INC., Seoul (KR)

( * ) Notice: Subject to any disclaimer, the term of this patent is extended or adjusted under 35 U.S.C. 154(b) by 0 days.

(21) Appl. No.: 17/967,537

(22) Filed: Oct. 17, 2022

(30) Foreign Application Priority Data

Apr. 25, 2022 (KR) ........................ 10-2022-0050802

(51) Int. Cl.
*G06K 9/00* (2022.01)
*A61K 35/12* (2015.01)
(Continued)

(52) U.S. Cl.
CPC .......... *G06T 7/0012* (2013.01); *A61B 5/0033* (2013.01); *A61B 5/441* (2013.01); *G06V 10/60* (2022.01); *G06V 40/161* (2022.01); *G06V 40/63* (2022.01); *G06T 2207/10152* (2013.01); *G06T 2207/30088* (2013.01); *G06T 2207/30201* (2013.01)

(58) Field of Classification Search
CPC .................................. G06K 9/00; A61K 35/12
USPC ........ 382/100, 103, 106–107, 108, 118, 128, 382/154, 162, 172, 173, 181, 189–191, 382/203, 209, 219, 224, 254, 276, 382/285–291, 295, 312, 321, 305, 274; 600/556

See application file for complete search history.

(56) References Cited

U.S. PATENT DOCUMENTS 9,058,765 B1 * 6/2015 Mallick .............. G06Q 30/0256
11,232,290 B2 * 1/2022 McDuff ............... A61B 5/1176
(Continued)

FOREIGN PATENT DOCUMENTS

KR 10-2019-0084771 A 7/2019
KR 10-2020-0004841 A 1/2020
(Continued)

OTHER PUBLICATIONS

Korean Notice of Result of Preliminary Examination of No. 10-2022-0050802 dated Jun. 8, 2022.
(Continued)

*Primary Examiner* — Seyed H Azarian
(74) *Attorney, Agent, or Firm* — Sughrue Mion, PLLC

(57) ABSTRACT

According to various embodiments, an image analysis server for determining whether an image is suitable for skin analysis may include a DB management unit for obtaining a captured image from a skin measurement device and storing the captured image; a user detector for detecting a user's face based on the obtained image; an image suitability determination unit for determining whether the obtained image is suitable for skin analysis; a skin analyzer for analyzing skin corresponding to the detected user's face based on the image determined to be suitable for skin analysis; and a service providing unit for calculating a skin score according to the analysis and providing the calculated skin score to a user terminal.

5 Claims, 7 Drawing Sheets

(51) Int. Cl.
*G06T 7/00* (2017.01)
*G06V 40/16* (2022.01)
*G06V 40/60* (2022.01)
*G06V 10/60* (2022.01)
*A61B 5/00* (2006.01)

(56) References Cited

U.S. PATENT DOCUMENTS

| | | | |
|---|---|---|---|
| 2019/0125249 A1* | 5/2019 | Rattner | A61B 5/0077 |
| 2020/0037882 A1* | 2/2020 | Westerhof | A61B 5/0077 |
| 2020/0383629 A1* | 12/2020 | Yoo | A61B 5/742 |
| 2022/0254189 A1* | 8/2022 | Dissanayake | A61B 5/748 |

FOREIGN PATENT DOCUMENTS

| | | |
|---|---|---|
| KR | 10-2020-0137918 A | 12/2020 |
| KR | 10-2020-0142938 A | 12/2020 |

OTHER PUBLICATIONS

Korean Notice of Allowance of No. 10-2022-0050802 dated Jul. 18, 2022.

* cited by examiner

[FIG. 1]
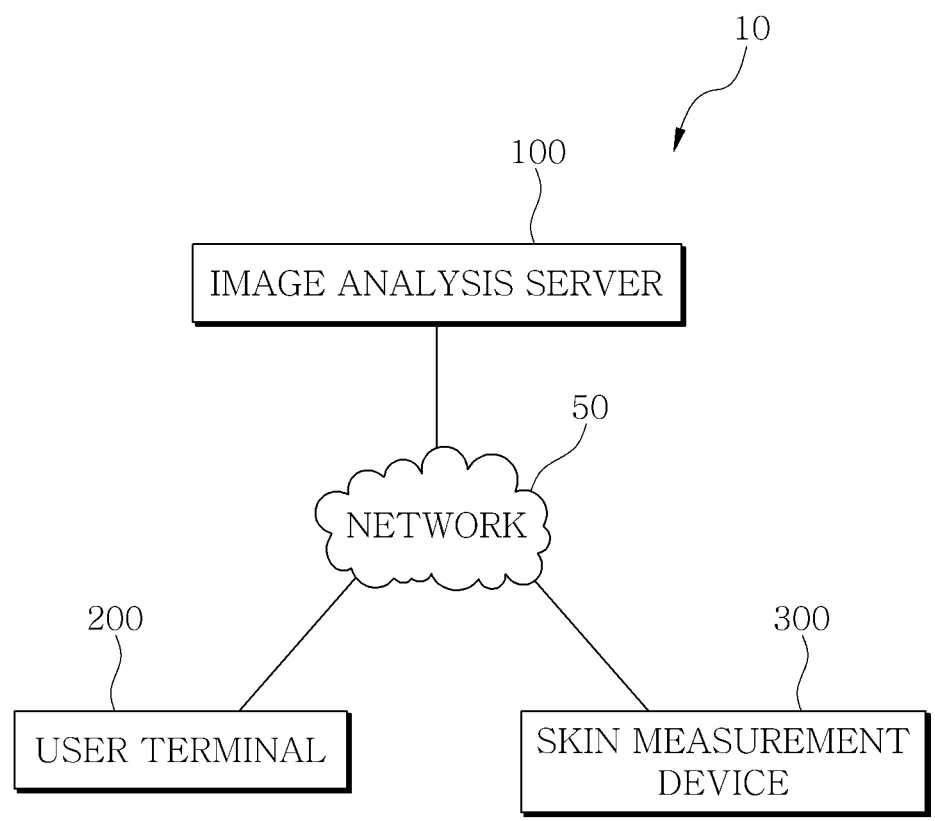

[FIG. 2]
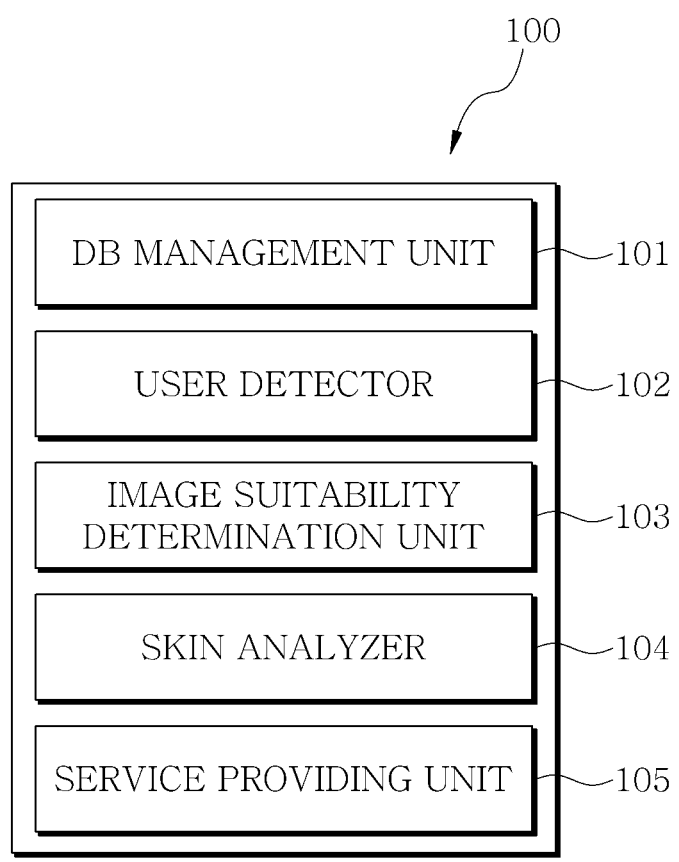

[FIG. 3]
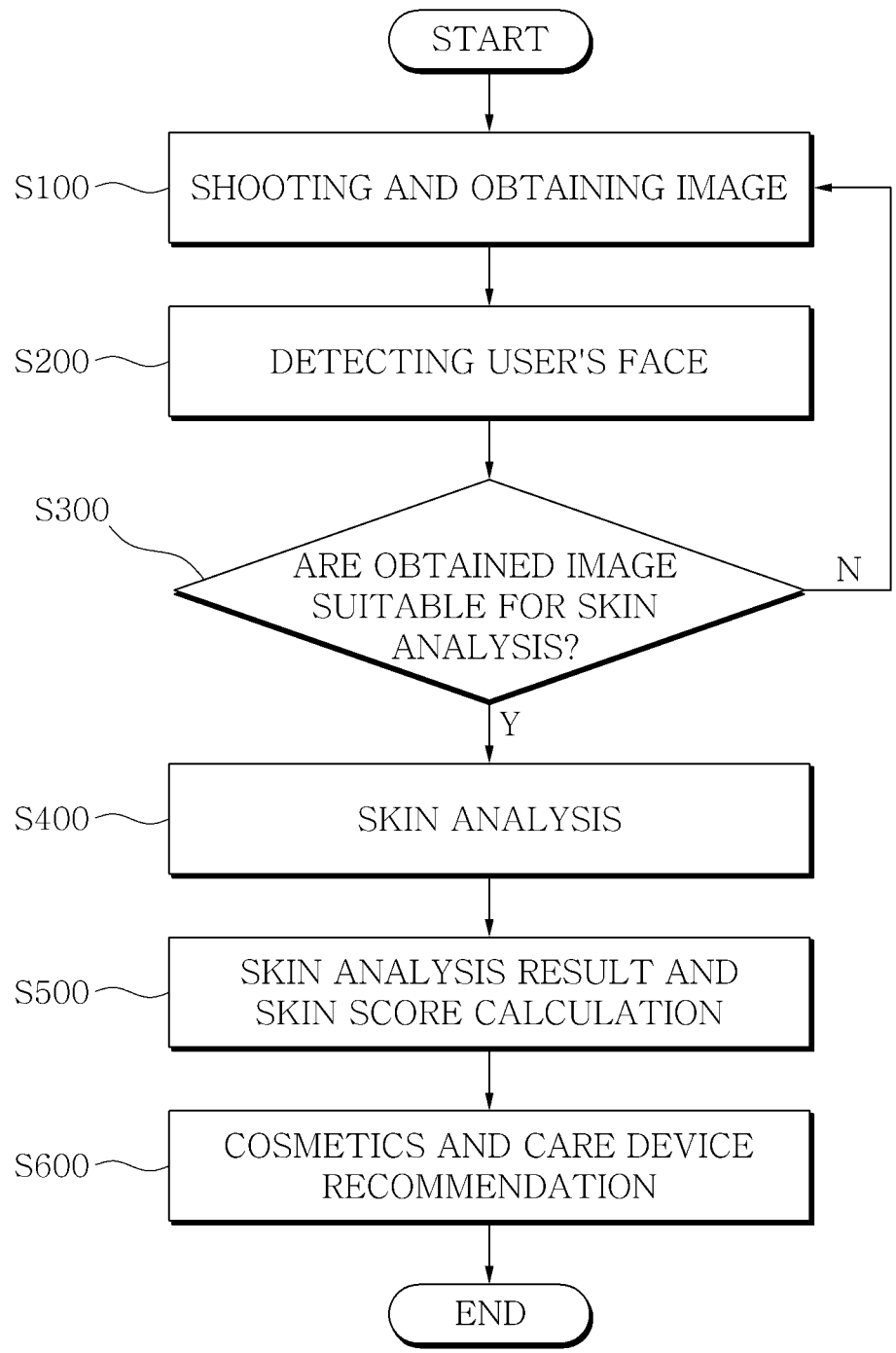

[FIG. 4]
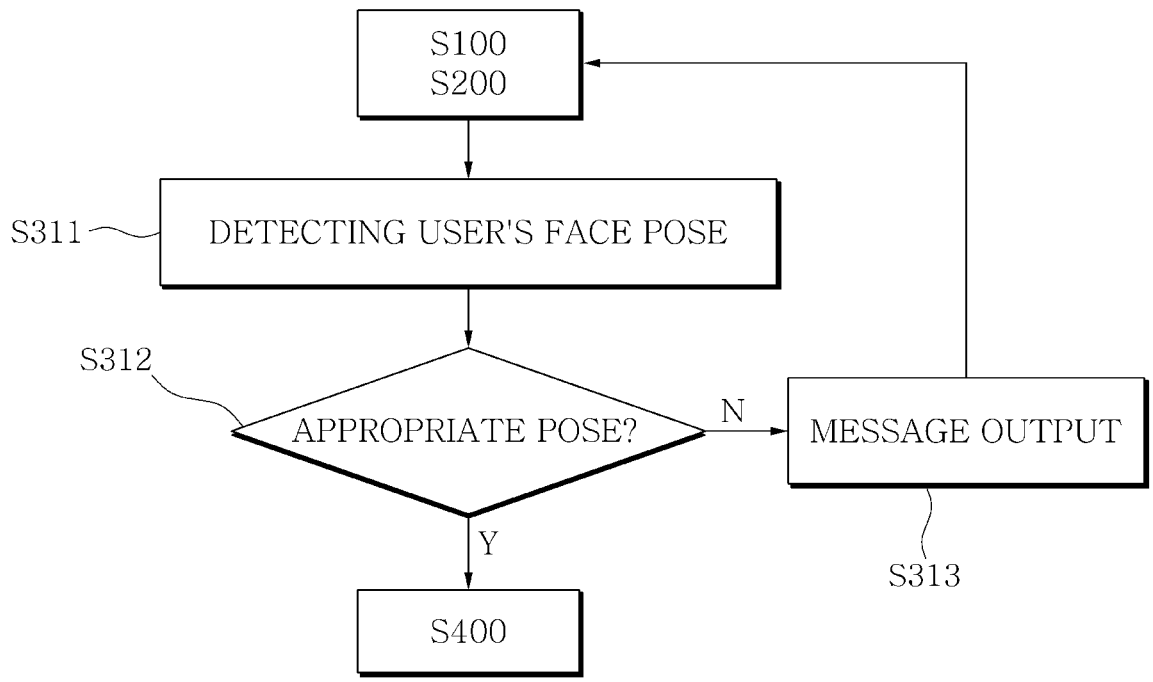
[FIG. 5]
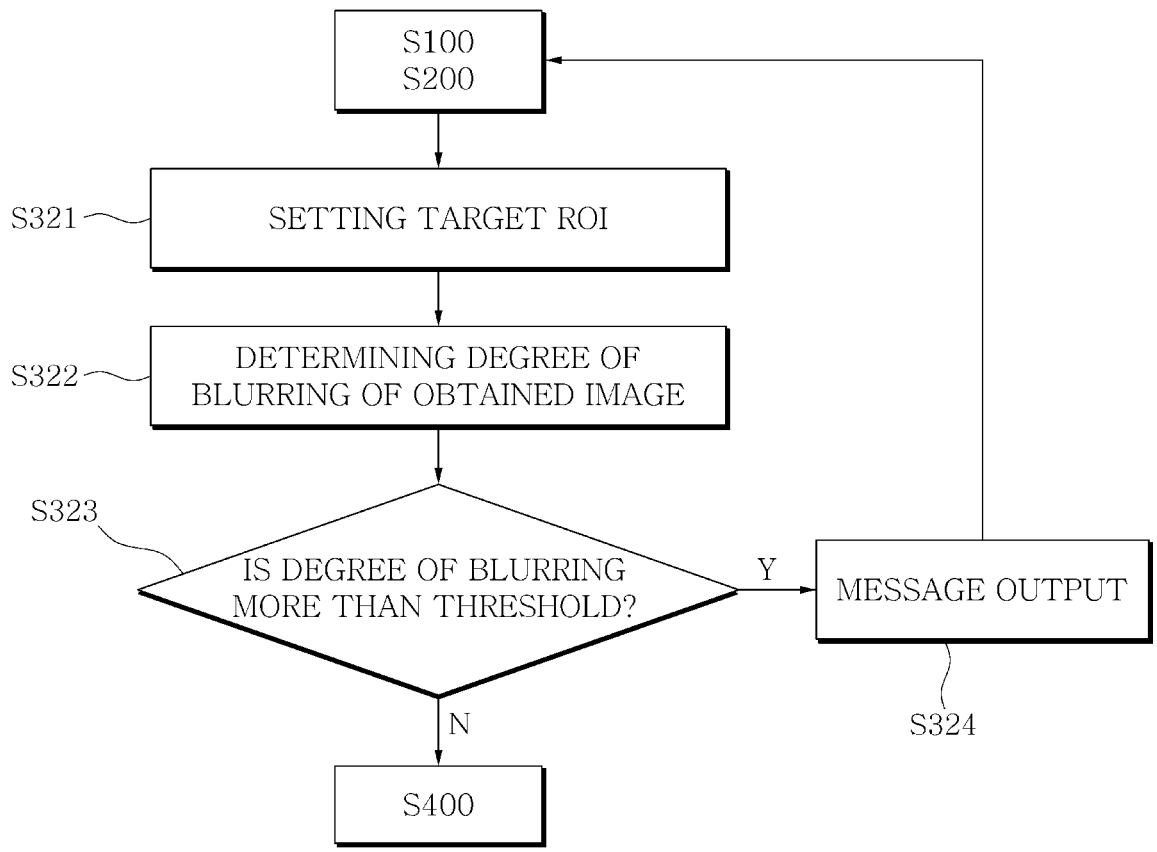

[FIG. 6]
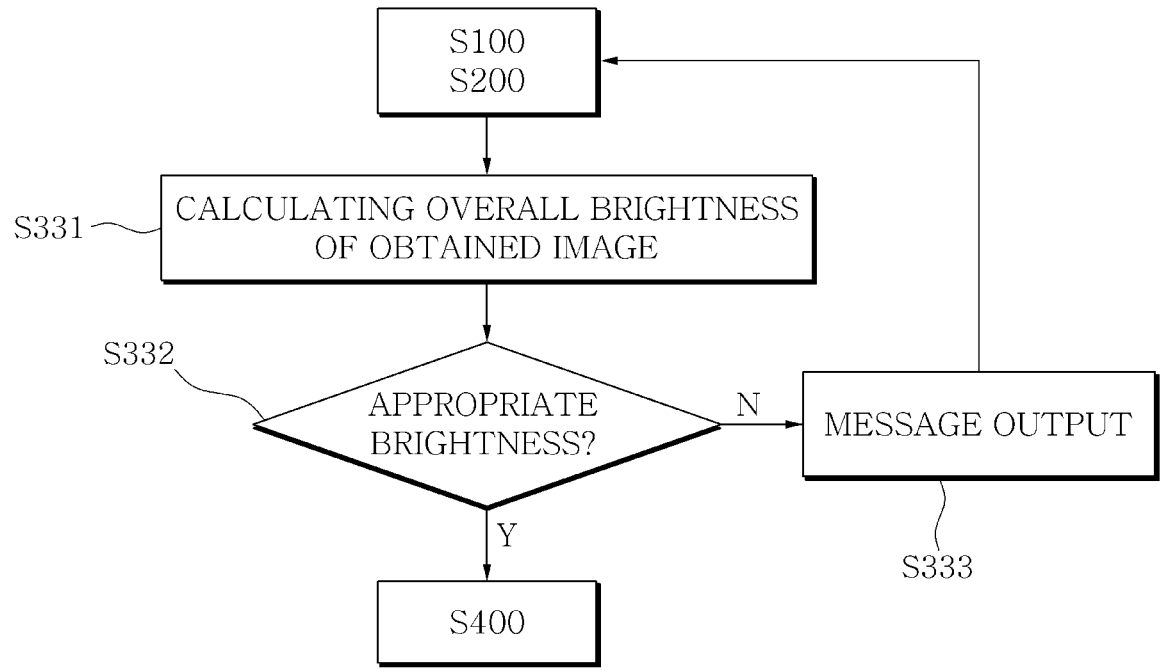
[FIG. 7]
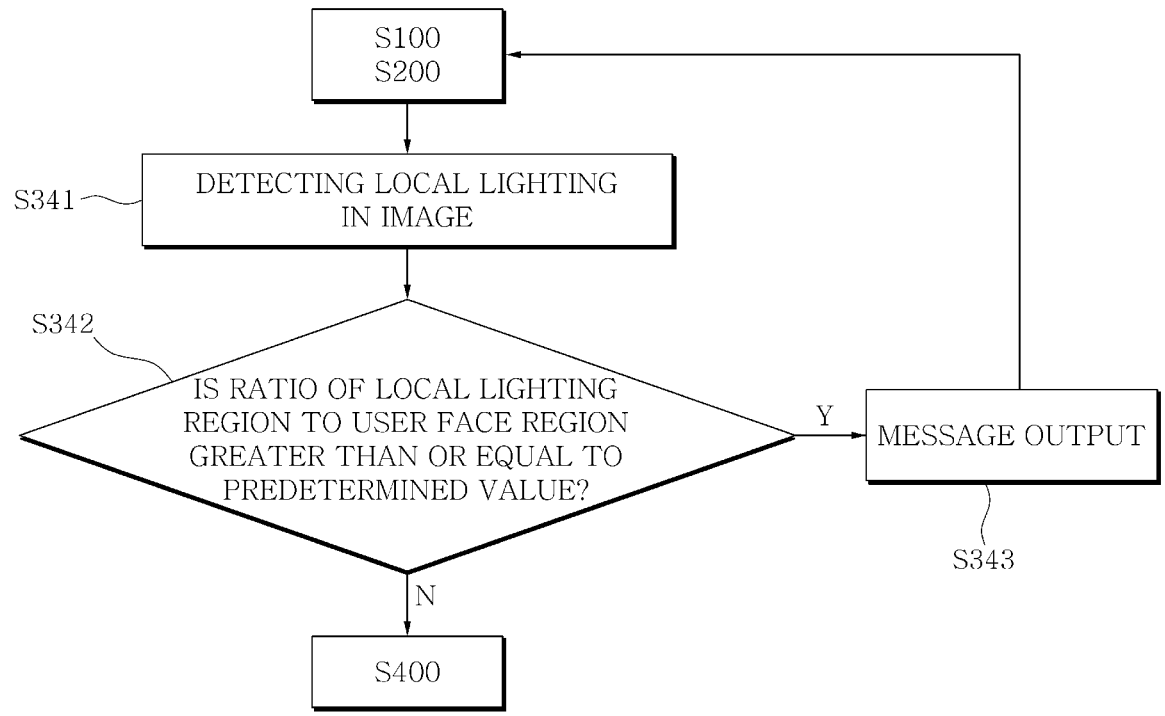

[FIG. 8]
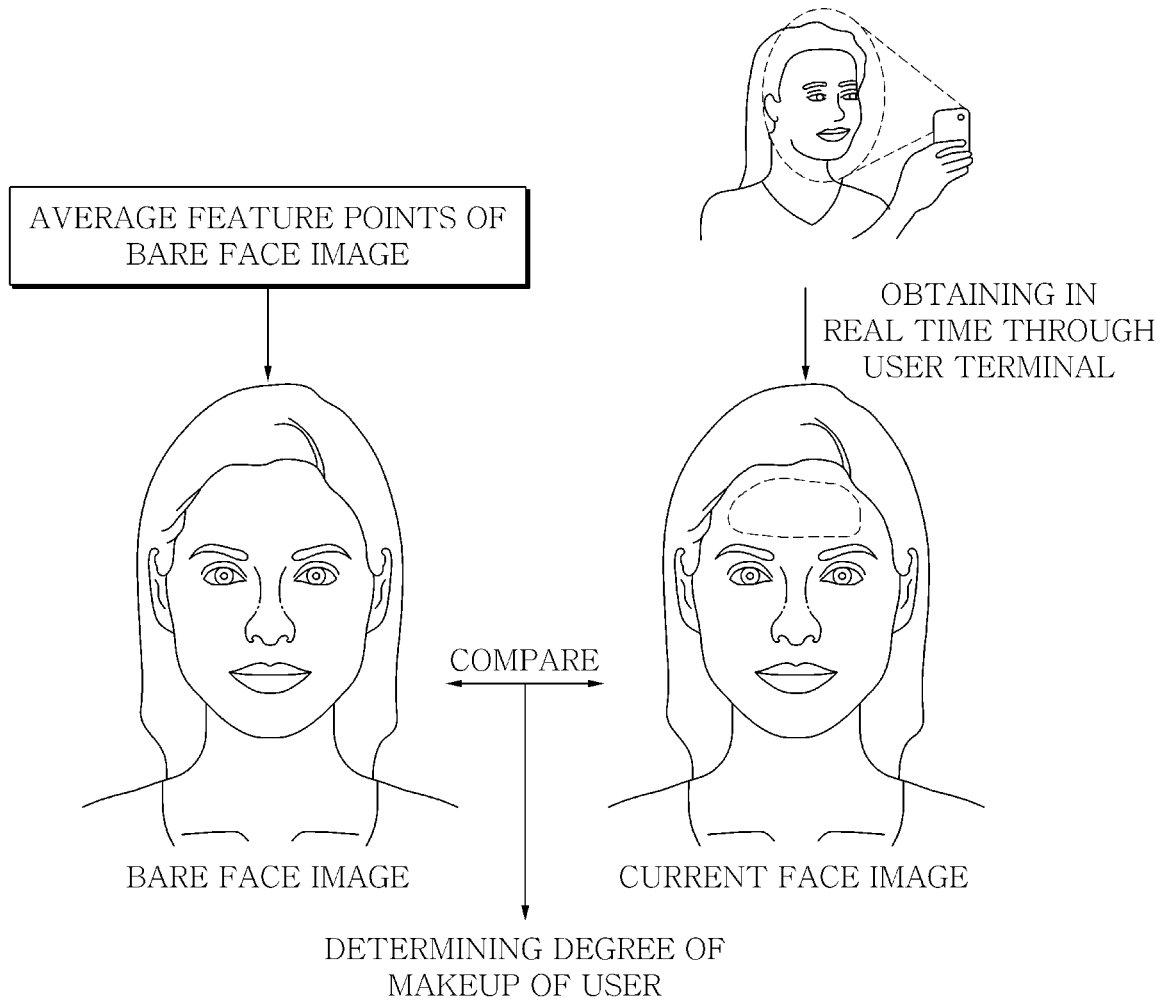
[FIG. 9]
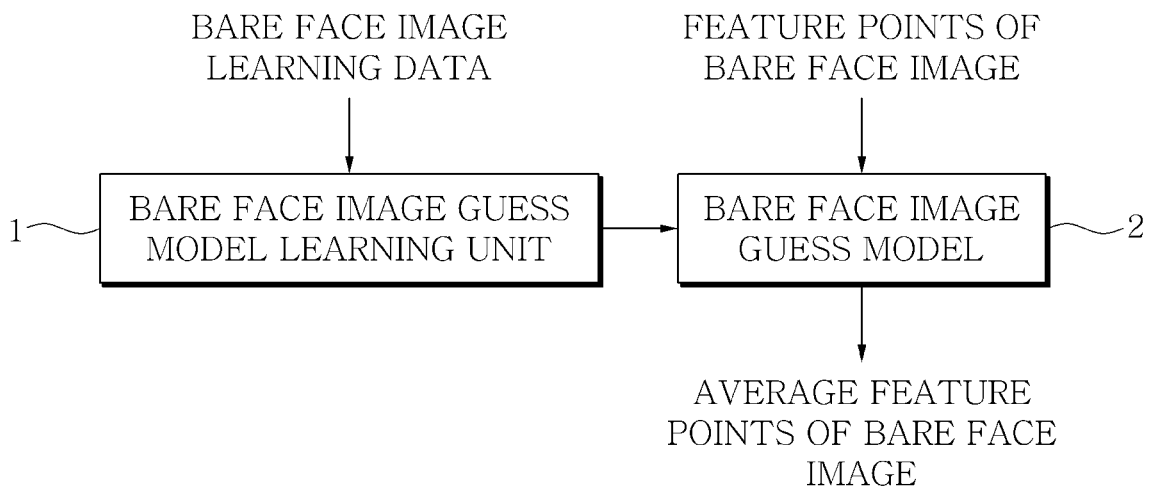

[FIG. 10]
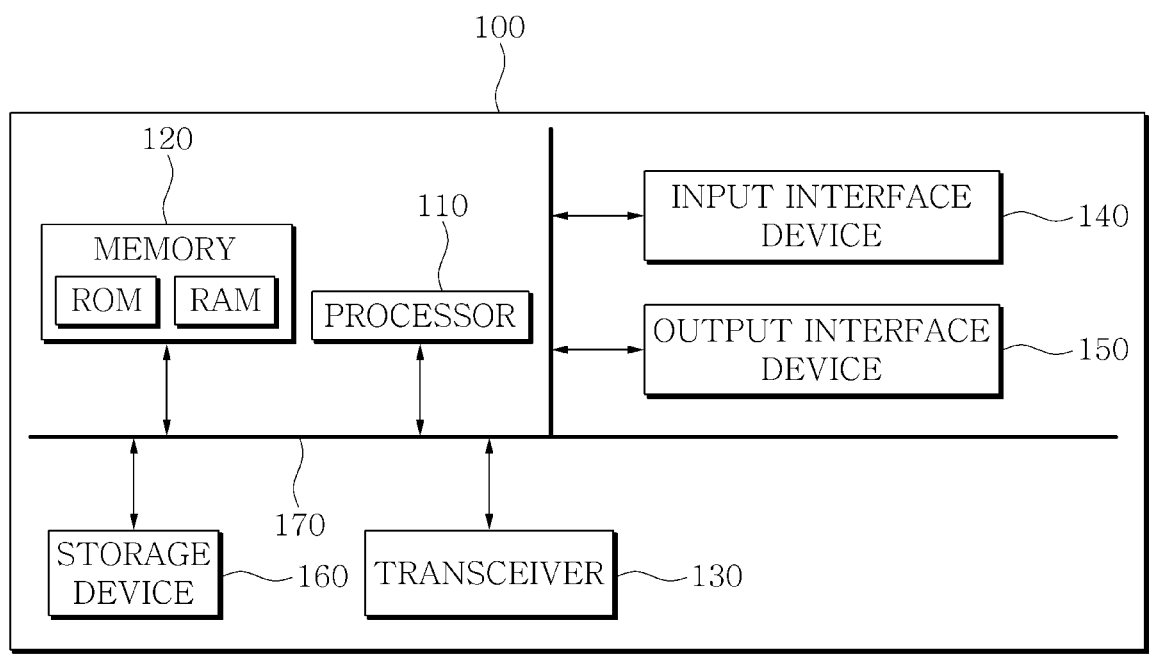

METHOD OF DETERMINING SUITABILITY OF SKIN ANALYSIS IMAGE AND APPARATUS THEREFOR

CROSS-REFERENCE TO RELATED APPLICATION

This application claims priority to Korean Patent Application No. 10-2022-0050802, filed on Apr. 25, 2022, in the Korean Intellectual Property Office, the disclosure of which is incorporated herein by reference.

BACKGROUND OF THE DISCLOSURE

Field of the Disclosure

The present disclosure relates to a method of determining suitability of a skin analysis image and an apparatus therefor.

Description of the Related Art

Unless indicated otherwise, this section does not describe prior art to the claims of this application. In addition, the technology included in this section is not considered prior art.

In recent years, as interest in beauty has increased, interest in facial skin care is also increasing. In particular, a method of photographing the user's facial skin and analyzing various skin troubles (e.g., wrinkles, pores, and acne) on the user's face and a portable device for measuring skin conditions are being developed.

In recent years, a skin care system including a skin condition measuring device has been used. The system recommends cosmetics, skin care devices, health functional foods, and the like based on skin condition measurement results. In particular, research and development for a system that measures skin conditions and recommends customized products based on IoT technology and big data is actively underway.

To measure and improve a user's skin condition, it is important to obtain an optimal skin image. Even when a facial image is inappropriate for skin analysis, cosmetics or care devices that are not suitable for the user may be recommended through a skin analysis algorithm based on the image. Accordingly, there is a need for a method of determining whether an input image is suitable for skin analysis before skin analysis.

SUMMARY OF THE DISCLOSURE

Therefore, the present disclosure has been made in view of the above problems, and it is an object of the present disclosure to provide a method of determining whether an input image is suitable for skin analysis based on several criteria and an apparatus therefor.

It is another object of the present disclosure to provide a consistent skin analysis score by excluding a region inappropriate for skin analysis from an input image or by reflecting a region inappropriate for skin analysis with a low weight.

In accordance with one aspect of the present disclosure, provided is an image analysis server for determining whether an image is suitable for skin analysis, the image analysis server including a DB management unit for obtaining a captured image from a skin measurement device and storing the captured image; a user skin analysis region detector for detecting a skin analysis region based on the obtained image; an image suitability determination unit for determining whether the obtained image is suitable for skin analysis; a skin analyzer for analyzing skin corresponding to the detected user skin analysis region based on the image determined to be suitable for skin analysis; and a service providing unit for calculating a skin score according to the analysis and providing the calculated skin score to a user terminal, wherein, when the skin analysis region is a face, the image suitability determination unit sets feature points in the he user skin analysis region, determines an orientation and angle of a face of the user based on the set feature points, and determines whether the image is suitable for skin analysis according to the orientation and angle of the user face; and when the image is not suitable for skin analysis, the image suitability determination unit transmits a message instructing re-photographing to the user terminal.

According to various embodiments, the image suitability determination unit may set a region of interest within the image and may determine a degree of blurring of the set region of interest. When the determined degree of blurring is greater than or equal to a preset threshold, the image suitability determination unit may determine that the image is not suitable for skin analysis.

According to various embodiments, the image suitability determination unit may convert the image to a grayscale image and extract a brightness value of the grayscale image. When the extracted brightness value is greater than or equal to a preset first brightness value, or the extracted brightness value is less than or equal to a preset second brightness value that is less than the first brightness value, the image suitability determination unit may determine that the obtained image is not suitable for skin analysis.

According to various embodiments, the image suitability determination unit may calculate an average brightness value of a user face region and an average brightness value of a background region in the image, and calculate a difference value between the average brightness value of the user face region and the average brightness value of the background region. When a brightness value of the image is less than the first brightness value and greater than the second brightness value, the image suitability determination unit may determine that the obtained image is suitable for skin analysis when the difference value is within a preset threshold range, and the image suitability determination unit may determine that the obtained image is not suitable for skin analysis when the difference value is out of the preset threshold range.

According to various embodiments, the service providing unit may calculate an individual score for each of items such as wrinkles, skin tone, pore state, pigmentation, dark circles, blush, and keratin state of a user's skin, provide the calculated individual score for each item to the user terminal, determine a sum of weights of the calculated individual scores as an overall score for the skin condition, and provide the determined overall score to the user terminal. As resolution of the image calculated based on a degree of blurring of the image decreases, the overall score may decrease.

According to various embodiments, the image suitability determination unit may calculate a first ratio between a blurred region and a non-blurred region in a user face region in the image and a second ratio between a blurred region and a non-blurred region in a background region in the obtained image. When the first ratio in the user face region is less than or equal to a preset first threshold ratio, and the second ratio in the background region is greater than or equal to a preset second threshold ratio, the image suitability determination unit may determine that the image is suitable for skin analysis.

According to various embodiments, the image suitability determination unit may detect local lighting in the user face region. When pixel values of a region in which local lighting is detected are oversaturated, the image suitability determination unit may determine that the image is not suitable for skin analysis. The image suitability determination unit may determine whether a ratio of the local lighting region to the user face region is greater than or equal to a predetermined value. The image suitability determination unit may calculate an average brightness value of the user face region, determine a region having a brightness value exceeding the average brightness value of the user face region, calculate a first area of the determined region, calculate an area ratio between the first area and a second area that is an area of the user face region. When the area ratio is greater than or equal to a first area ratio, the image suitability determination unit may transmit a message instructing re-photographing to the user terminal. When the area ratio is less than the first area ratio and is greater than or equal to a second area ratio that is less than the first area ratio, the image suitability determination unit may determine a region excluding a region corresponding to the first area in the user face region as a skin analysis target region. When the area ratio is less than the second area ratio, the image suitability determination unit may determine that the image is suitable for skin analysis.

According to various embodiments, the image analysis server may further include a bare face determination unit. The image suitability determination unit may determine a degree of makeup of a user based on a current face image of the user and a bare face image of the user. When the degree of makeup exceeds a preset reference value, the image suitability determination unit may determine that the obtained image is not suitable for skin analysis. The bare face image guess model may be subjected to supervised-learning in advance using training data including a first feature vector obtained by transforming feature points of a bare face image obtained by targeting a large number of people as an input value and a second feature vector obtained by transforming feature points of an average bare face image obtained for the people as an output value. The bare face determination unit may generate a bare face image of the user using the bare face image guess model that has been subjected to supervised-learning, may convert feature points of the bare face image of the user into an input vector and input the input vector into the bare face image guess model, may convert an output vector obtained as output of the bare face image guess model and obtain average feature points of the bare face image of the user, and may use the feature points of the bare face image of the user to generate a bare face image of the user.

According to various embodiments, the image analysis server may further include a makeup degree determination unit. The makeup degree determination unit may compare the bare face image and a current face image of the user to determine a degree of makeup of the user. The makeup degree determination unit may determine a degree of trouble change and a degree of color change for each partial region in the bare face image of the user and the current face image of the user, determine the degree of makeup of the user based on the degree of trouble change and the degree of color change, and determine an index indicating the degree of makeup through the following equation.

$$y = \sum_{j=1}^{j=h}\left(\left(\sum_{k=1}^{k=p}\sqrt{(jk_n - jk_m)^3}\right) \times w_1 + \left(\sqrt{(jc_n - jc_m)^3}\right) \times w_2\right)$$

In the equation, y is an index indicating the degree of makeup, p is the number of types of troubles, c is a degree of change in color value, h is the number of the partial regions, $w_1$ is a weight for the trouble, $w_2$ is a weight for the skin color, n is an index for a bare face image, and m is an index for a current face image.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a diagram illustrating an image analysis system according to one embodiment;

FIG. 2 is a diagram illustrating major components constituting an image analysis server;

FIG. 3 is a flowchart related to providing a user skin analysis service according to one embodiment;

FIG. 4 is a flowchart related to determining whether an obtained image is suitable for skin analysis based on a user's face pose;

FIG. 5 is a flowchart related to determining whether an obtained image is suitable for skin analysis based on the degree of blurring of the image;

FIG. 6 is a flowchart related to determining whether an obtained image is suitable for skin analysis based on the degree of brightness of the image;

FIG. 7 is a flowchart related to determining whether an obtained image is suitable for skin analysis based on local lighting detected in the image;

FIG. 8 is a diagram related to determining whether an obtained image is suitable for skin analysis depending on user's makeup and the degree of makeup;

FIG. 9 is a diagram for explaining a bare face image guess model according to one embodiment; and FIG. 10 is a diagram illustrating the hardware configuration of the image analysis server according to FIG. 1.

DETAILED DESCRIPTION OF THE DISCLOSURE

Since the present disclosure may be applied with various modifications and may have various embodiments, exemplary embodiments and drawings of the present disclosure are intended to be explained and exemplified. However, these exemplary embodiments and drawings are not intended to limit the embodiments of the present disclosure to particular modes of practice, and all changes, equivalents, and substitutes that do not depart from the spirit and technical scope of the present disclosure should be understood as being encompassed in the present disclosure. Like reference numerals refer to like elements in describing each drawing.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present disclosure. As used herein, the term "and/or" includes any or all combinations of one or more of the associated listed items.

It should be understood that when an element is referred to as being "connected to" or "coupled to" another element, the element may be directly connected or coupled to the other element or intervening elements may be present. In contrast, when an element is referred to as being "directly connected to" or "directly coupled to" another element, there are no intervening elements present.

The terms used in the present specification are used to explain a specific exemplary embodiment and not to limit the present inventive concept. Thus, the expression of singularity in the present specification includes the expression of plurality unless clearly specified otherwise in context. Also, terms such as "include" or "comprise" should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments according to the present disclosure will be described in detail with reference to the accompanying drawings.

FIG. 1 illustrates an image analysis system 10 according to one embodiment. Referring to FIG. 1, the image analysis system 10 may include an image analysis server 100 and a user terminal 200.

The operations described below may be implemented by a server 100 and/or a skin measurement device 300, and may also be implemented by the user terminal 200. That is, the operations performed by a DB management unit 101, a user detector 102, an image suitability determination unit 103, a skin analyzer 104, and a service providing unit 105 to be described below may be understood as modules operated by a processor included in the user terminal 200. An image captured by the skin measurement device 300 may be replaced with an image captured by a camera module included in the user terminal 200. That is, the server 100 is described as one operating subject as an example of hardware performing a software operation, and it will be apparent at the level of a person skilled in the art that such an operating subject may be the user terminal 200.

Alternatively, as another example, the operations described below may be performed or implemented through a platform (e.g., a web page and/or an application) controlled by the server 100. That is, the server 100 may provide a website in which a user accesses the server 100 through a network using the user terminal 200 to input, register, and output various information. The server 100 may provide an application capable of inputting, registering, and outputting various information by being installed and executed in the user terminal 200.

The user terminal 200 may be a device or apparatus having a communication function, such as a desktop computer, a laptop computer, a notebook, a smartphone, a tablet PC, a mobile phone, a smart watch, a smart glass, an e-book reader, a portable multimedia player (PMP), a handheld game console, a navigation device, a digital camera, a digital multimedia broadcasting (DMB) player, a digital audio recorder, a digital audio player, a digital video recorder, a digital video player, or a personal digital assistant (PDA).

The skin measurement device 300 may be a camera module, and may be a separate camera device or a camera device mounted on the user terminal 200. The skin measurement device 300 may include a lens assembly, a flash, an image sensor, an image stabilizer, a memory (e.g., a buffer memory), and/or an image signal processor.

The lens assembly may collect light emitted from an object to be photographed. The lens assembly may include one or more lenses. According to one embodiment, the skin measurement device 300 may include a plurality of lens assemblies. For example, the skin measurement device 300 may form a dual camera, a 360 degree camera, or a spherical camera. Some of the lens assemblies may have the same lens properties (e.g., angle of view, focal length, autofocus, f number, or optical zoom), or at least one lens assembly may have one or more lens properties different from lens properties of other lens assemblies.

For example, the lens assembly may include wide angle lens or telephoto lens. The flash may emit light that is used to enhance light emitted or reflected from a subject. The flash may include one or more light-emitting diodes (e.g., a red-green-blue (RGB) LED, a white LED, an infrared LED, or an ultraviolet LED), or may include a xenon lamp. The image sensor may obtain an image corresponding to a subject by converting light that is emitted or reflected from the subject and transmitted through a lens assembly into an electrical signal. According to one embodiment, for example, the image sensor may include an image sensor selected from among image sensors with different properties, such as an imageable specific spectral sensor, such as an RGB sensor, a black and white (BW) sensor, an IR sensor, or a UV sensor, a plurality of image sensors having the same properties, or a plurality of image sensors having different properties. For example, each image sensor included in the image sensor may be implemented using a charged coupled device (CCD) sensor or a complementary metal oxide semiconductor (CMOS) sensor.

In response to movement of the skin measurement device 300 and/or the user terminal 200 including the skin measurement device 300, the image stabilizer may move at least one lens included in a lens assembly and/or an image sensor in a specific direction or control operation characteristics (e.g., read-out timing, etc.) of the image sensor. Through this adjustment, at least a part of the negative effect of the movement on an image being photographed may be compensated. The image stabilizer may use a gyro sensor and/or an acceleration sensor disposed inside or outside the skin measurement device 300 to detect move of the skin measurement device 300 and/or the user terminal 200 including the skin measurement device 300. For example, the image stabilizer may be implemented as an optical image stabilizer. The memory may at least temporarily store at least a portion of images obtained through an image sensor for a next image processing operation. For example, when image acquisition is delayed due to shutter operation, or a plurality of images is obtained at high-speed, an obtained original image (e.g., a Bayer-patterned image or a high resolution image) may be stored in the memory, and the corresponding copy image (e.g., a low resolution image) may be previewed through a display device. Thereafter, when a specified condition is satisfied (e.g., a user input or a system command), at least a portion of the original image stored in the memory may be acquired and processed by, for example, an image signal processor.

The server 100, the user terminal 200, and the skin measurement device 300 may be connected to a communication network 50, respectively, and may transmit/receive data to and from each other through the communication network 50. For example, as the communication network 50, various wired or wireless networks such as a local area network (LAN), a metropolitan area network (MAN), Global System for Mobile Network (GSM), Enhanced Data GSM Environment (EDGE), High-Speed Downlink Packet Access (HSDPA), Wideband Code Division Multiple Access (W-CDMA), Code Division Multiple Access (CDMA), Time Division Multiple Access (TDMA), Bluetooth, Zigbee, Wi-Fi, Voice over Internet Protocol (VoIP), LTE Advanced, IEEE802.16m, WirelessMAN-Advanced, HSPA+, 3GPP Long Term Evolution (LTE), Mobile WiMAX (IEEE 802.16e), UMB (formerly EV-DO Rev. C), Flash-OFDM, iBurst and MBWA (IEEE 802.20) systems, HIPERMAN, Beam-Division Multiple Access (BDMA), World Interoperability for Microwave Access (Wi-MAX), and 5G may be used.

FIG. 2 is a diagram illustrating major components constituting the image analysis server 100, and FIG. 3 is a flowchart related to providing a user skin analysis service according to one embodiment.

The DB management unit 101 may obtain an image captured by the skin measurement device 300 and/or a user terminal on which the skin measurement device 300 is mounted (S100). The DB management unit 101 may store the obtained image. The DB management unit 101 may store face images of each of a plurality of users.

The user detector 102 may detect a subject (e.g., a user's face) through analysis of an obtained image (S200). The user detector 102 may detect a user's face and parts related to a user's face (e.g., eyes, nose, mouth, ears, and the like). In addition, the user detector 102 may detect a user's body, body-related parts (e.g., arms, legs, neck, and the like), and gestures. The user detector 102 may detect at least one subject using various detection methods. The user detector 102 may detect a user using artificial intelligence such as machine learning. For example, the user detector 102 may detect a user's face using a segmentation technique (e.g., upper body segmentation). The various detection methods are not limited to specific methods, and may include various previously disclosed methods.

The image suitability determination unit 103 may determine whether an obtained image is suitable for skin analysis (S300). The image suitability determination unit 103 determines whether a user's face pose is appropriate, whether an image is blurry, whether the brightness value of an image is appropriate, whether there are other objects overlapped in a user's face area, and whether skin analysis is difficult due to local lighting. Based on these results, the image suitability determination unit 103 may determine whether an obtained image is suitable for skin analysis. For example, when a user's face is covered by other objects, the image suitability determination unit 103 may determine that the obtained image is not suitable for skin analysis. Specifically, when hair, glasses, and/or hands are detected in a user's face area, the image suitability determination unit 103 may determine that an obtained image is not suitable for skin analysis. Detailed description thereof may be further described with reference to the drawings below.

The image suitability determination unit 103 may perform skin analysis according to user settings from the viewpoint of convenience even when inappropriate. To maintain the accuracy of analysis results, the image suitability determination unit 103 may determine for each local region and adjust a skin analysis score based on the skin analysis suitability of the local region so as to maintain the consistency of the skin analysis score. The image suitability determination unit 103 may calculate skin analysis suitability, and may transmit a message regarding the limit of skin analysis to the user terminal 200 based on the calculated skin analysis suitability.

The skin analyzer 104 may analyze the user's skin based on the image determined to be suitable for skin analysis (S400). The skin analyzer 104 may perform pre-processing before analyzing the user's skin based on the image. The pre-processing process may include 3A processing, lens shading correction, edge enhancement, dead pixel correction, and knee correction. The 3A processing may include at least one of auto white balance (AWB), auto exposure (AE), and auto focusing (AF). In addition, the pre-processing process may include at least one of index change and tuning parameter change. The skin analyzer 104 may adjust the contrast, sharpness, saturation, and dithering of an image through the pre-processing process. Here, the adjustment of contrast, sharpness, and saturation may be performed in a YUV color space, and the dithering procedure may be performed in a red-green-blue (RGB) color space.

The service providing unit 105 may provide a skin analysis result to the user terminal 200, calculate a skin score according to the skin analysis result, and provide the calculated skin score to the user terminal 200 (S500). The service providing unit 105 may recommend cosmetics and/or skin care devices capable of improving a user's skin according to the skin analysis result (S600).

FIG. 4 is a flowchart related to determining whether an obtained image is suitable for skin analysis based on a user's face pose.

The image suitability determination unit 103 may detect a user's face pose from an obtained image (S311). The image suitability determination unit 103 may determine whether the detected user's face pose is suitable for skin analysis (S312).

The image suitability determination unit 103 may determine whether a user's face pose (e.g., orientation, angles) is included in preset reference poses. When a user's face pose is included in the preset reference poses, the image suitability determination unit 103 may determine that an obtained image is suitable for skin analysis.

The image suitability determination unit 103 may detect feature points within a detected user's face and identify a user's face pose (e.g., orientation, angles, and the like) based on the feature points. The image suitability determination unit 103 may determine whether the image is taken from the front side, from the right side, or from the left side.

For example, when a user's left eye, right eye, left ear, right ear, nose, chin, and mouth are detected, the image suitability determination unit 103 may determine that the obtained image was taken from the front. The image suitability determination unit 103 may identify a user's face pose (e.g., orientation, angles) in the image. When a user's face angle is within a preset first angle range in the vertical direction (e.g., 10 degrees in the vertical direction) and is within a preset second angle range in the horizontal direction (e.g., 15 degrees in the horizontal direction), the image suitability determination unit 103 may determine that the image is suitable for skin analysis.

For example, when a user's left eye, left ear, nose, chin, and mouth are detected, the image suitability determination unit 103 may determine that an obtained image was taken from the left side. The image suitability determination unit 103 may identify a user's face pose (e.g., orientation, angles) in the image. When a user's face angle is within a preset third angle range in the vertical direction (e.g., 10 degrees in the vertical direction) and is within a preset fourth angle range in the left direction (e.g., 20 to 30 degrees in the left direction), the image suitability determination unit 103 may determine that the image is suitable for skin analysis.

For example, when a user's right eye, right ear, nose, chin, and mouth are detected, the image suitability determination unit 103 may determine that an obtained image was taken from the right side. The image suitability determination unit 103 may identify a user's face pose (e.g., orientation, angles) in the image. When a user's face angle is within a preset fifth angle range in the vertical direction (e.g., 10 degrees in the vertical direction) and is within a preset sixth angle range in the right direction (e.g., 20 to 30 degrees in the right direction), the image suitability determination unit 103 may determine that the image is suitable for skin analysis.

When a user's face pose detected in an obtained image is not suitable for skin analysis, the image suitability determination unit 103 may output a message instructing re-photographing (S313).

FIG. 5 is a flowchart related to determining whether an obtained image is suitable for skin analysis based on the degree of blurring of the image.

The image suitability determination unit 103 may determine whether an obtained image is blurry. When an obtained image is determined to be blurry, the image suitability determination unit 103 may determine that the obtained image is not suitable for skin analysis.

The image suitability determination unit 103 may set a region of interest (ROI) in an obtained image (S321). For example, the image suitability determination unit 103 does not simply determine whether the obtained image is blurry. The image suitability determination unit 103 may divide the obtained image into a plurality of regions. When only regions unrelated to skin analysis (e.g., background regions other than a user's face) are blurred, the image suitability determination unit 103 does not determine that the image is blurry. When a region related to skin analysis (e.g., a user face region) is blurry, the image suitability determination unit 103 may determine that the obtained image is blurry.

The image suitability determination unit 103 may determine the degree of blurring of an obtained image (S322). The image suitability determination unit 103 may analyze frequency components of the obtained image to detect a blurred region and a non-blurred region in the image.

The image suitability determination unit 103 may determine whether the degree of blurring is greater than or equal to a preset threshold (S323). The image suitability determination unit 103 may calculate a first ratio between a blurred region and a non-blurred region in a user face region in an obtained image, and may calculate a second ratio between a blurred region and a non-blurred region in a background region in the obtained image. When the first ratio in the user face region is less than or equal to a preset first threshold ratio, and the second ratio in the background region is greater than or equal to a preset second threshold ratio, the image suitability determination unit 103 may determine that the image is suitable for skin analysis.

Based on an obtained image, the image suitability determination unit 103 may identify a case wherein blurring is caused by an error in a camera AF focus function, a case wherein blurring is caused by movement of a user (subject), and the like to determine whether the image is blurry.

When an obtained image is determined to be blurry, the image suitability determination unit 103 may output a message instructing re-photographing (S324). Based on a re-photographed image, when the image is determined to be unsuitable for skin analysis according to the degree of blurring (e.g., 2 times in a row), the image suitability determination unit 103 may adjust a reference value for the degree of blurring downward.

FIG. 6 is a flowchart related to determining whether an obtained image is suitable for skin analysis based on the degree of brightness of the image.

The image suitability determination unit 103 may calculate a brightness value of the entire region of an obtained image (S331), and may determine whether the brightness value is appropriate (S332). For example, when the brightness value of the obtained image is above a threshold value (i.e., when the image is bright) or below a threshold value (i.e., when the image is dark), the image suitability determination unit 103 may determine that the obtained image is not suitable for skin analysis.

The image suitability determination unit 103 may convert the image into a color space independent of a user's overall skin color detected through the color value of the obtained image. For example, the image suitability determination unit 103 may convert the image into a grayscale image and extract a brightness value (e.g., a luminance value) of the converted grayscale image. When an extracted brightness value of a user face region is greater than or equal to a preset first brightness value or is less than or equal to a preset second brightness value that is lower than the first brightness value, the image suitability determination unit 103 may determine that an obtained image is not suitable for skin analysis. That is, when an extracted brightness value is less than the first brightness value and is greater than the second brightness value, the image suitability determination unit 103 may determine that an obtained image is suitable for skin analysis.

The image suitability determination unit 103 may calculate an average brightness value of a user face region and an average brightness value of a background region in an image. The image suitability determination unit 103 may calculate a difference value between the average brightness value of the user face region and the average brightness value of the background region. When a brightness value of an image is less than the first brightness value and greater than the second brightness value, and the difference value is within the preset threshold range, the image suitability determination unit 103 may determine that the obtained image is suitable for skin analysis. When the difference value is out of the difference value, the image suitability determination unit 103 may determine that the obtained image is not suitable for skin analysis.

As a result of calculating a brightness value of an entire image, when an obtained image is determined to be unsuitable for skin analysis, the image suitability determination unit 103 may output a message instructing re-photographing (S333).

FIG. 7 is a flowchart related to determining whether an obtained image is suitable for skin analysis based on local lighting detected in the image.

The image suitability determination unit 103 may detect local lighting in a user face region (S341). The image suitability determination unit 103 may identify a case in which a portion of a user face region is oversaturated or undersaturated by local illumination. For example, when local lighting is detected in the corresponding regions due to the protruding portions of a user's face (forehead, nose bridge, cheekbone, etc.), and the pixel values of the corresponding regions are oversaturated, skin analysis based on the image may be determined to be difficult.

The image suitability determination unit 103 may determine whether the ratio of a local lighting region to a user face region is greater than or equal to a predetermined value (S342). The image suitability determination unit 103 may calculate an average brightness value of the user face region and determine a region having a brightness value exceeding the average brightness value of the user face region. The image suitability determination unit 103 may calculate a first area of a determined region and calculate an area ratio between the first area and a second area that is an area of the user face region. When the area ratio is greater than or equal to a first area ratio, the image suitability determination unit 103 may output a message instructing re-photographing (S343). When the area ratio is less than the first area ratio and is greater than or equal to a second area ratio, the image suitability determination unit 103 may determine a region excluding a region corresponding to the first area in the user face region as a skin analysis target region. The second area ratio may be less than the first area ratio.

FIG. 8 is a diagram related to determining whether an obtained image is suitable for skin analysis depending on user's makeup and the degree of makeup. FIG. 9 is a diagram for explaining a bare face image guess model according to one embodiment. For example, when user's makeup is heavy, user skin analysis based on an input image is highly unlikely to be accurate, and thus the input image may be determined as an unsuitable image.

The image suitability determination unit 103 may determine whether a user is wearing makeup and/or the degree of makeup. When the user's makeup degree exceeds a preset reference value, the image suitability determination unit 103 may determine that the obtained image is not suitable for skin analysis.

The image suitability determination unit 103 may determine the degree of makeup of a user based on a current face image and bare face image of a user. The current face image may be a user's face image obtained in real time from the skin measurement device 300. For example, the current face image may be a face image in which a user's face is detected based on an obtained image. The bare face image may be a face image without makeup obtained from the user terminal 200, and may be an image obtained by estimating an image of a user's face without makeup based on an input image including the user's face based on deep learning. For example, the bare face image may be a face image determined through feature points of a user's face image using a pre-trained artificial neural network.

The image suitability determination unit 103 may compare a bare face image of a user with a current face image of the user, and may determine the degree of makeup of the user based on change in skin color, change in the number of troubles (e.g., change in the size of dark circles, change in the number of red spots, and change in the number of freckles), and the like.

The bare face determination unit 1031 may determine, as a bare face image, a face image having feature points obtained as an output of an artificial neural network from among bare face images of a user stored in the DB management unit 101. Alternatively, the artificial neural network-based bare face determination unit 1031 may determine, as an average face image, a face image most similar to a face image having feature points obtained as an output of an artificial neural network among face images of a user stored in the DB management unit 101.

Referring to FIG. 9, the artificial neural network-based bare face determination unit 1031 may include a bare face image guess model learning unit 1 and a bare face image guess model 3. The bare face image guess model learning unit 1 and the bare face image guess model 3 are configured according to the functions of the artificial neural network-based bare face determination unit 1031, and may perform all functions of the artificial neural network-based bare face determination unit 1031.

The artificial neural network-based bare face determination unit 1031 may obtain bare face image learning data stored in the DB management unit 101. The bare face image learning data according to an embodiment may be training data having the feature point of a bare face image as an input value and the average feature point of a face image as an output value. The feature point of a face image may be a color value corresponding to each pixel.

The bare face image guess model learning unit 1 may obtain, as learning data, the bare face images of users corresponding to each of a plurality of user terminals from the user terminals. The bare face image guess model learning unit 1 may learn a bare face image guess model by using the obtained learning data. An artificial neural network may be used as the bare face image guess model 3 according to an embodiment. The artificial neural network is a prediction model implemented in software or hardware that mimics the computational power of a biological system using a large number of artificial neurons (or nodes).

The bare face image guess model 3 may be subjected to supervised learning using the feature points of a bare face image and the average feature points of a bare face image by the bare face image guess model learning unit 1. In this case, supervised learning refers to learning to find an output value according to a given input value using data having an input value and an output value corresponding thereto as learning data, and means learning performed in a state where a correct answer is known. The set of input and output values given to supervised learning is called training data. That is, the above-described 'feature points of a bare face image' and 'average feature points of a bare face image' are input values and output values, respectively, and may be used as training data for supervised learning of the bare face image guess model 3.

For example, the bare face image guess model learning unit 1 may convert the feature points of a bare face image into a unique first one-hot vector to generate an input value, may convert the average feature points of the bare face image into a unique second one-hot vector to generate an output value, and then may perform supervised learning on the bare face image guess model 3 using the generated input and output values. Here, the first one-hot vector and the second one-hot vector may be vectors in which one of vector component values is '1' and the other component values are '0'.

In one embodiment, the bare face image guess model 3 may include an input layer that receives input values and has nodes corresponding to the number of components of a first one-hot vector; one or more hidden layers for multiplying each output value of the input layer by connection strength (or weight) and adding a bias to the multiplication result to output the result; and an output layer for multiplying each output value of the hidden layers by connection strength (or weight) and outputting the result using an activation function. For example, the activation function may be an LeRU function or a Softmax function, without being limited thereto. Connection strength and bias may be continuously updated by supervised learning.

Specifically, the bare face image guess model 3 may be subjected to supervised learning such that an output value of a loss function according to a given input value (first one-hot vector) and output value (second one-hot vector) is minimized. For example, the loss function (H(Y, Y')) may be defined as in Equation 1 below.

$$H(Y, Y') = -\sum_{m=1}^{V} Y_m \cdot \log(Y_m^*) \quad \text{[Equation 1]}$$

In Equation 1, $Y_m$ may be the m-th component of a second one-hot vector, and $Y'_m$ may be the m-th component of an output vector output by receiving a first one-hot vector from the bare face image guess model 3.

A makeup degree determination unit 1032 may compare a bare face image with a current face image of a user to determine the degree of makeup of the user. The makeup degree determination unit 1032 may determine the degree of makeup of a user for each partial region in a user's estimated bare face image and a user's current face image. For example, the makeup degree determination unit 1032 may determine the degree of makeup of a user for each partial region of the user, such as a forehead, a nose, eye regions, eyebrows, lips, and cheeks, in the bare face image and the current face image.

$$y = \sum_{j=1}^{j=h}\left(\left(\sum_{k=1}^{k=p}\sqrt{(jk_n - jk_m)^3}\right) \times w_1 + \left(\sqrt{(jc_n - jc_m)^3}\right) \times w_2\right) \quad \text{[Equation 2]}$$

In Equation 2, y is an index indicating the degree of makeup, p is the number of types of troubles, c is the degree of change in color value, h is the number of the partial regions, $w_1$ is a weight for the trouble, $w_2$ is a weight for the skin color, n is an index for a bare face image, and m is an index for a current face image.

The makeup degree determination unit 1032 may calculate the degree of change of trouble and the degree of color change for each partial region in a bare face image and a current face image, and may determine the degree of makeup of a user based on the calculated trouble change degree and color change degree. The degree of change of trouble may be calculated based on a difference in the number of troubles detected by comparing a bare face image with a user's current face image. The degree of color change may be calculated based on change values of R (red pixel), G (green pixel), and B (blue pixel) values, which are pixel values for each partial region.

When the degree of makeup of a user exceeds a preset first reference value, the image suitability determination unit 103 may output a caution message (e.g., a message that skin analysis may not be accurate), and may perform skin analysis based on an obtained image. Alternatively, the image suitability determination unit 103 may output a request message asking whether to continue skin analysis. When an input signal indicating user acceptance according to the request message is received, the image suitability determination unit 103 may perform skin analysis based on an obtained image.

When the degree of makeup of a user exceeds a preset second reference value that is greater than the first reference value, the image suitability determination unit 103 may output a warning message (e.g., a message indicating that skin analysis is not possible) or a message instructing re-photographing.

FIG. 10 illustrates the hardware configuration of the image analysis server 100 of FIG. 1.

Referring to FIG. 10, the image analysis server 100 may include at least one processor 110 and a memory storing instructions instructing the processor 110 to perform at least one operation.

The at least one operation may include at least some of the operations or functions of the image analysis server 100 described above, and may be implemented in the form of instructions and performed by the processor 110.

The processor 110 may mean a central processing unit (CPU), a graphics processing unit (GPU), or a dedicated processor on which methods according to embodiments of the present disclosure are performed. Each of a memory 120 and a storage device 160 may be configured as at least one of a volatile storage medium and a non-volatile storage medium. For example, the memory 120 may be one of a read only memory (ROM) and a random access memory (RAM), and the storage device 160 may include a flash-memory, a hard disk drive (HDD), a solid state drive (SSD), various memory cards (e.g., a micro SD card), or the like.

In addition, the image analysis server 100 may include a transceiver 130 that performs communication through a wireless network. In addition, the server 100 may further include an input interface device 140, an output interface device 150, the storage device 160, and the like. Components included in the image analysis server 100 may be connected to each other by a bus 170 to perform communication. In FIG. 10, the image analysis server 100 has been described as an example, but the present disclosure is not limited thereto. For example, a plurality of user terminals may include the component according to FIG. 10.

According to various embodiments of the present disclosure, a case in which an input image is not suitable for skin analysis due to various external situations and carelessness of a user can be determined in advance.

In addition, according to various embodiments, when an image is not suitable for skin analysis, overall skin analysis performance can be improved by taking measures in advance.

In addition, according to various embodiments, by not using an inappropriate image for skin analysis, malfunctions can be prevented in advance, and unnecessary processes can be omitted.

In addition, various effects recognized directly or indirectly through the present specification can be provided.

The methods according to the embodiments of the present disclosure may be implemented in the form of a program command that can be executed through various computer means and recorded in a computer-readable medium. The computer-readable medium can store program commands, data files, data structures or combinations thereof. The program commands recorded in the medium may be specially designed and configured for the present disclosure or be known to those skilled in the field of computer software.

Examples of a computer-readable recording medium include hardware devices such as ROMs, RAMs and flash memories, which are specially configured to store and execute program commands. Examples of the program commands include machine language code created by a compiler and high-level language code executable by a computer using an interpreter and the like. The hardware devices described above may be configured to operate as one or more software modules to perform the operations of the embodiments, and vice versa.

In addition, all or part of the configuration or function of the above-described method or apparatus may be implemented in combination or implemented separately.

Although the present disclosure has been described above with reference to the embodiments of the present disclosure, those skilled in the art may variously modify and change the present disclosure without departing from the spirit and scope of the present disclosure as set forth in the claims below.

DESCRIPTION OF SYMBOLS

100: IMAGE ANALYSIS SERVER
200: USER TERMINAL
300: SKIN MEASUREMENT DEVICE

What is claimed is:

1. An image analysis server for determining whether an image is suitable for skin analysis, comprising:
    a database management unit performed by a processor for obtaining a captured image from a skin measurement device and storing the captured image;
    a user skin analysis region detector for detecting a skin analysis region based on the obtained image;
    an image suitability determination unit performed by a processor for determining whether the obtained image is suitable for skin analysis;
    a skin analyzer for analyzing skin corresponding to the detected user skin analysis region based on the image determined to be suitable for skin analysis; and
    a service providing unit performed by a processor for calculating a skin score according to the analysis and providing the calculated skin score to a user terminal,
    wherein, when the skin analysis region is a face of the user, the image suitability determination unit performed by a processor determines whether the image is suitable for skin analysis;
    when the image is not suitable for skin analysis, the image suitability determination unit performed by a processor transmits a message instructing re-photographing to the user terminal;
    the image suitability determination unit performed by a processor calculates a first ratio between a blurred region and a non-blurred region in a user face region in the obtained image and a second ratio between a blurred region and a non-blurred region in a background region in the obtained image;
    when the first ratio in the user face region is less than or equal to a preset first threshold ratio, and the second ratio in the background region is greater than or equal to a preset second threshold ratio, the image suitability determination unit performed by a processor determines that the image is suitable for skin analysis;
    the image suitability determination unit performed by a processor detects local lighting in the user face region;
    when pixel values of a local lighting region in which local lighting is detected are oversaturated, the image suitability determination unit performed by a processor determines that the image is not suitable for skin analysis;
    the image suitability determination unit performed by a processor determines whether a ratio of the local lighting region to the user face region is greater than or equal to a predetermined value;
    the image suitability determination unit performed by a processor calculates an average brightness value of the user face region, determines a region having a brightness value exceeding the average brightness value of the user face region, calculates a first area of the determined region, calculates an area ratio between the first area and a second area that is an area of the user face region;
    when the area ratio is greater than or equal to a first area ratio, the image suitability determination unit performed by a processor transmits a message instructing re-photographing to the user terminal;
    when the area ratio is less than the first area ratio and is greater than or equal to a second area ratio that is less than the first area ratio, the image suitability determination unit performed by a processor determines a region excluding a region corresponding to the first area in the user face region as a skin analysis target region; and
    when the area ratio is less than the second area ratio, the image suitability determination unit performed by a processor determines that the image is suitable for skin analysis.

2. The image analysis server according to claim 1, wherein the image suitability determination unit sets a region of interest within the image and determines a degree of blurring of the set region of interest,
    wherein, when the determined degree of blurring is greater than or equal to a preset threshold, the image suitability determination unit performed by a processor determines that the image is not suitable for skin analysis.

3. The image analysis server according to claim 2, wherein the image suitability determination unit performed by a processor extracts a brightness value of the image,
    wherein, when the extracted brightness value is greater than or equal to a preset first brightness value, or the extracted brightness value is less than or equal to a preset second brightness value that is less than the first brightness value, the image suitability determination unit performed by a processor determines that the obtained image is not suitable for skin analysis.

4. The image analysis server according to claim 3, wherein the image suitability determination unit performed by a processor calculates an average brightness value of a user face region and an average brightness value of a background region in the image, and calculates a difference value between the average brightness value of the user face region and the average brightness value of the background region,
    wherein, when a brightness value of the image is less than the first brightness value and greater than the second brightness value,
    the image suitability determination unit performed by a processor determines that the obtained image is suitable for skin analysis when the difference value is within a preset threshold range, and
    the image suitability determination unit performed by a processor determines that the obtained image is not suitable for skin analysis when the difference value is out of the preset threshold range.

5. The image analysis server according to claim 1, wherein the image suitability determination unit performed by a processor compares a current face image of the user and a bare face image of the user to determine a degree of makeup of the user,
    wherein, when the degree of makeup exceeds a preset first reference value, the image suitability determination unit performed by a processor determines that the obtained image is not suitable for skin analysis, and the image suitability determination unit performed by a processor outputs a caution message indicating that skin analysis may be inaccurate when performing skin analysis using the image determined to be unsuitable, or outputs a request message asking whether to perform skin analysis using the image determined to be unsuitable; and when the degree of makeup exceeds a preset second reference value that is greater than the first reference value, the image suitability determination unit performed by a processor outputs a warning message indicating that skin analysis is not possible with the image determined to be unsuitable, or outputs a message instructing re-photographing.

* * * * *